United States Patent [19]

Oka et al.

[11] Patent Number: 5,458,643
[45] Date of Patent: * Oct. 17, 1995

[54] ARTIFICIAL INTERVERTEBRAL DISC

[75] Inventors: Masanori Oka, Nara; Shokyu Gen; Yoshito Ikada, both of Uji; Hideaki Okimatsu, Kyoto, all of Japan

[73] Assignees: Kyocera Corporation; Kabushiki Kaisha Biomaterial Universe Corporation of Japan, both of Kyoto, Japan

[ * ] Notice: The portion of the term of this patent subsequent to May 24, 2011 has been disclaimed.

[21] Appl. No.: 189,603

[22] Filed: Feb. 1, 1994

Related U.S. Application Data

[62] Division of Ser. No. 692,202, Apr. 26, 1991, Pat. No. 5,314,478.

[30] Foreign Application Priority Data

Mar. 29, 1991 [JP] Japan ................................. 3-92699

[51] Int. Cl.⁶ ........................... A61F 2/30; A61F 2/44
[52] U.S. Cl. ........................ 623/18; 623/17; 623/23
[58] Field of Search ............................ 623/16, 17, 18, 623/20, 22, 23, 66

[56] References Cited

U.S. PATENT DOCUMENTS

| | | | |
|---|---|---|---|
| 4,073,999 | 2/1978 | Bryan et al. | 623/66 |
| 4,220,152 | 9/1980 | Dresback | 623/66 |
| 4,220,153 | 9/1980 | Dresback | 623/66 |
| 4,634,720 | 1/1987 | Dorman et al. | 623/16 |
| 4,664,669 | 5/1987 | Ohyabu et al. | 623/11 |
| 4,693,986 | 9/1987 | Vit et al. | 623/16 |
| 4,778,471 | 10/1988 | Bajpai | 623/16 |
| 4,813,965 | 3/1989 | Roberts | 623/16 |
| 4,938,778 | 7/1990 | Ohyabu et al. | 623/12 |
| 4,990,163 | 2/1991 | Ducheyene et al. | 623/16 |
| 5,007,930 | 4/1991 | Dorman et al. | 623/16 |

FOREIGN PATENT DOCUMENTS

| | | |
|---|---|---|
| 0061744 | 4/1983 | Japan . |
| 2215461 | 1/1993 | Japan . |
| 6316948 | 1/1993 | Japan . |
| 6470041 | 1/1993 | Japan . |
| 6476851 | 1/1993 | Japan . |
| 6330758 | 1/1993 | Japan . |

*Primary Examiner*—David Isabella
*Attorney, Agent, or Firm*—Spensley Horn Jubas & Lubitz

[57] ABSTRACT

A prosthesis used for a damaged bone, an artificial articular cartilage or an artificial intervertebral disc being characterized in that the prosthesis is a composite body comprising polyvinyl alcohol hydrogel and ceramic or metallic porous body. With this prosthesis, PVA hydrogel enhances lubrication and shock absorbing functions, and the porous body allows the ingrowth and ossification of the bone tissue of a living body therein to affinitively connect said hydrogel to the bones of the living body.

3 Claims, 4 Drawing Sheets

ARTIFICIAL INTERVERTEBRAL DISC

This is a division of application Ser. No. 07/692,202, filed on Apr. 26, 1991, now U.S. Pat. No. 5,314,478.

BACKGROUND OF THE INVENTION

1. Field of the Invention

The present invention relates to a prosthesis, more specifically an artificial bone connection prosthesis used for the replacement of damaged bones, an articular cartilage such as a coxa and a knee joint, and a spine's intervertebral disc.

In the disclosure described below, the invention relating to the articular cartilage is described as a first invention and the invention relating to the intervertebral discs is described as a second invention.

2. Prior Art

At present, even if an articular cartilage is partially damaged, it is replaced with an artificial articular cartilage since there is no appropriate surgical treatment method. The artificial articular cartilage is greatly beneficial to patients who are suffering from joint trouble. However, serious problems, such as complications caused by the replacement of artificial joints, in particular a high occurrence rate of loosening problems and the necessity of another operation due to the breakage of the bones around the artificial joints.

The artificial joints which are currently used are made of hard materials such as metals and ceramics and a soft socket made of ultra-polymer high-density polyethylene (HDPE). This HDPE is superior in tear resistance, but it is inferior in wear resistance and shock absorbing performance for impact load. Reaction of foreign matter caused by powder generated due to wear is also causing problems.

An articular cartilage is located on the surface of a bone joint. The articular cartilage of the knee joint or coxa of a human being is 2 to 4 mm in thickness. The articular cartilage absorbs shock applied by the weight of the human being and distributes and transmits the impact load to a chondral cancellous bone trabeculation to play an important role of allowing smooth movability under low friction. One of the most important features of the articular cartilage is its high extracellular water content, 60% to 80%. The elasticity and lubrication of the articular cartilage are brought by this high water content.

So far, various materials, such as HDPE, polyhydroxyethyl methacrylate (PHEMA) gel, silicone and polyvinyl alcohol (PVA) gel, have been examined as the materials for the artificial articular cartilage, but they were insufficient in their dynamic characteristics.

The materials of the artificial articular cartilage must meet the requirements listed below:

i) Superior affinity to a human body ii) Chemical and physical stability iii) Superior dynamic characteristics (wear resistance, shock absorbing effect, lubrication, etc.)

As described above, conventional artificial articular cartilages have drawbacks in characteristics regarding lubrication, shock absorbing and wear resistance.

On the other hand, an intervertebral disc is located between individual vertebral bodies. More specifically, two vertebral bodies and an intervertebral disc located therebetween comprise a motion segment: a function unit at the spine. The disc comprises sturdy fiber Pings which surround the outer circumference of the nucleus pulposus made of fiber cartilage with alternately arranged collagen fiber bundles, liquefied soft nucleus pulposus which holds the tension state of the intervertebral disc made of colloidal gel including much glycosaminoglycan bonded to water, and the end plate of cartilage which is made of glassy cartilage and is used to separate the vertebral body from the above-mentioned elements.

In our daily life, the intervertebral disc is subjected to complicated load which is a combination of compression, bending and distortion. When the spine is bent forward, stretched and bent sideways, stresses, in particular, tension and compression stresses occur on the disc. When the spine is turned, shearing stress occurs on the disc. The load applied to the nucleus pulposus in the intervertebral disc is uniformly distributed in a normal case and exerts force hydrostatically. Therefore, the intervertebral disc has a hydrostatic Function at its motion segment. The disc thus has very important roles; it functions as a cushion between vertebral bodies, stores energy and absorbs shock of load by distributing the load. In addition, the disc is greatly related to the internal stability together with ligaments.

If the intervertebral disc having the above-mentioned important functions is damaged by a disease such as the hernia of the intervertebral disc, the damaged disc is treated as described below at present. The deformed intervertebral disc is taken out first. Then, a self transplantation bone, bone cement or an artificial vertebral body spacer is mainly used to fix the portion between the vertebral bodies.

However, all means, including the self transplantation bone, artificial vertebral body made of stainless steel, alumina ceramics and hydroxy apatite, bone cement made of polymethyl methacrylate or a combination of these, are used only to fix the connection between vertebral bodies without considering the dynamic characteristics inherent to the intervertebral disc of a living body. The flexibility and shock absorbing function inherent to the intervertebral disc are disregarded. In particular, the upper and lower sections adjacent to the intervertebral disc are adversely affected in the living body dynamics, thereby frequently causing secondary problems at the sections adjacent to the intervertebral disc.

In addition to the above-mentioned technologies practiced actually, the prior arts disclosed so far are: "Artificial vertebral body spacer" (Japanese Provisional Patent Publication No. 84-78851) comprising a metal mesh unit with an elasticity close to that of the bone and being characterized in the method of fixing the unit to the upper and lower vertebral bodies, "Artificial intervertebral disc for a cervical vertebra (Japanese Provisional Patent Publication No. B3-164948) attaching importance to the motion of the intervertebral disc, "Artificial vertebral body" (Japanese Provisional Patent Publication No. B3-300758) aiming for substitution of the dynamic characteristics of the intervertebral disc, "Artificial intervertebral disc capsule and its embedding method" (Japanese Provisional Patent Publication No. 64-70041) and "Intervertebral disc prosthesis" (Japanese Provisional Patent Publication No. 2-215461).

The various artificial intervertebral discs devised so far are only artificial vertebral body spacers used just to substitute self transplantation bones and had no dynamic characteristics of the intervertebral disc of the living body, or have insufficient internal stability as a result that too much importance is placed to mobility. Even composite body discs aimed to substitute the dynamic characteristics of the intervertebral disc, made of flexible polymer material mainly at the inner sections and comprising hard materials, such as ceramic powder material or bioactive fibers, at the sections contacting bones cannot sufficiently substitute the softness and shock absorbing function of the intervertebral disc of the living body, cannot be sufficiently fixed to the bones or cannot have sufficient mechanical strength of itself. In this way, these composite body discs cannot satisfy the above-mentioned overall functions at the same time as artificial intervertebral discs.

SUMMARY OF THE INVENTION

The object of the first invention is to obviate the defects in the materials for the above-mentioned conventional artificial articular cartilages, that is, to improve the dynamic characteristics of an artificial articular cartilage and the method for connecting and fixing the artificial articular cartilage to the tissue of a living body.

The object of the second invention is to eliminate the problems in the above-mentioned conventional intervertebral discs.

The concepts of the first and second inventions are common in that the hydrogel of polyvinyl alcohol is used to improve the dynamic characteristics of the prosthesis and that the hydrogel is also used, in combination with ceramics or metallic porous bodies harmless to the living body, as a carrier to allow ingrowth and ossification of the bone tissue of the living body to improve the connection and fixation to the living tissue. The hydrogel of PVA is combined with the porous body and positioned at the dynamic interface between the living bones to provide excellent lubrication and shock absorbing characteristics. On the other hand, the tissue of the living body grows and ossificates into the porous body so that the prosthesis can achieve affinitive connection to the tissue of the living body. In this way, the prosthesis of the first invention has a significant adaptability as an articular cartilage and the prosthesis of the second invention also has a significant adaptability as an interverbral disc.

DETAILED DESCRIPTION OF THE INVENTION

Figure 1:
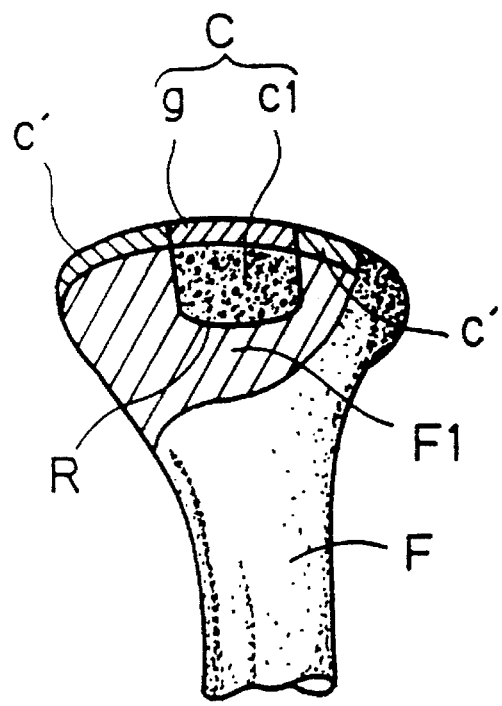
FIG. 1 is a schematic view illustrating the artificial articular cartilage of the first invention installed in a living body.

The inventors of the present invention earnestly studied to provide a prosthesis with excellent lubrication and shock absorbing characteristics of the articular cartilage of a living body and to make the prosthesis securely fixed to the tissue of a living body. As a result, the inventors have found that the above-mentioned objects can be achieved by combining PVA hydrogel with porous ceramics or titanium mesh, which are superior in affinity with the bones of a living body. More specifically, in the case of the artificial articular cartilage of the first invention, PVA hydrogel is carried via infiltration and fixation in part or most of the pores in the porous alumina ceramics or titanium mesh. By this method, the dynamic secure fixation is made between the members to be connected. In addition, the tissue of the living body ossificates into the non-infiltration/fixation section of the PVA hydrogel, thereby achieving secure connection and fixation as well as dynamic stability and adaptability to the living body for an extended period of time.

The artificial articular cartilage of the first invention is produced by the method described below. A PVA solution with a polymerization rate of 1700 or more and a saponification rate of 99.5 mol % is carried via infiltration in part or at an end of the porous alumina ceramics or titanium mesh. The solution is then subjected to a gelatinization process and set to get at low temperature. The PVA is then dried and heat-treated at a high temperature between 120° and 180° C.

With the artificial articular cartilage produced as described above, the PVA hydrogel functions as the articular cartilage of the living body, and the porous alumina ceramics or titanium mesh assures connection and fixation between the tissue of the living body and the PVA hydrogel.

The first invention will be specifically described below.

The PVA used with the present invention should have a saponification rate of 95 mol % or more, preferably 97 mol % of mope, most preferably 99 mol % or mope. If the saponification rate is lower than those values, the gel is apt to have less strength. The average polymerization rate should be 1700 or more at an average viscosity, preferably 3500 or more. As the polymerization rate becomes lower, the strength of the gel also becomes lower. The starting material of the PVA should be subjected to molecular distillation to prevent PVA with low molecular weight from eluting.

When the PVA solution is obtained, only water can be used as solvent. However, it is preferable to use solvent mixed with organic solvent which is affinitive to water. Examples of the organic solvents affinitive to water are dimethyl glycol (DMSO), ethylene glycol (EG), glycerol (GC), propylene glycol (PG), propylene alcohol (POH), ethyl alcohol (EOH), 1,3-dimethyl-imidazolizinone (DMI). The solvent can be a mixture of two or more types.

With the present invention, it is preferable to select DM80 from among the above-mentioned organic solvents by considering the solubility to the PVA, the ratio of mixture with water and the drop of the freezing point.

The mixture ratio between water and the above-mentioned solvent can be determined as desired, but normally should be in the range of 5:95 to 95:5.

In the present invention, the PVA solution is first adjusted and prepared. Its concentration should be in the range of 2 to 30 weight % depending on the desired strength and water content. To adjust and prepare such a solution, PVA is generally heated and dissolved. Only heating while stirring is possible or dissolution is possible by using an auto-clave or a microwave oven.

The completely dissolved PVA solution is then carried via infiltration into the porous alumina ceramics or titanium mesh. In order to carry the PVA hydrogel via fixation only at the desired portions, cyanic acrylate (instantaneous adhesive) or gelatin is filled in the portions where the living body tissue is desired for ossification. After the fixation, the PVA solution is carried via infiltration left at low temperature less than room temperature. The solution is set to gel, thereby making an artificial articular cartilage made of the PVA hydrogel. In the process, the solution is set to gel in a shorter period of time as the temperature is lower. The process should thus be conducted in a freezer at a temperature of −10° C. or less, preferably −20° C. or less.

The obtained PVA gel comprising a large amount of water and organic solvent is dried and heat-treated at high temperature. This heat treatment process can be done in the air, but preferably be conducted in vacuum, nitrogen gas flow or silicone oil. The heat treatment temperature should be 100° C. or more where the crystallization of the PVA can be promoted, preferably 120° to 180° C. The sufficient heat treatment time is normally 1 to 10 hours depending on the heating temperature.

Since the water content of the PVA hydrogel artificial articular cartilage made as described above can be greatly changed between 10 to 60 weight %, the desired dynamic characteristics can be obtained by adjusting the water content.

FIG. 1 is a schematic view illustrating the artificial articular cartilage (for a coxa) of the first invention installed in a living body. An articular cartilage C of the present invention is embedded in recess R disposed at the top end of femur F. PVA hydrogel g of the articular cartilage C is disposed to fit for cartilage C' of the living body. Porous alumina ceramics C1 with no hydrogel g is embedded in subchondral bone F1 of femur F.

The second invention:

To eliminate the defects of the above-mentioned intervertebral discs, the inventors of the present invention studied and experimented variously. Consequently, the inventors provide an artificial intervertebral disc comprising a pair of metallic or ceramic porous bodies and a polyvinyl alcohol hydrogel block incorporated therebetween.

(Examples)

The first and second inventions will be described further taking examples. However, the technical concepts of the present invention are not limited only to the examples.

Example 1

(Corresponding to the first invention)
(Preparation and adjustment of a PVA solution)

10 g of PVA with a polymerization rate of 5000 and a saponification rate of 99.9 mol % was added to 90 g of dimethyl sulfoxide/water mixture solvent (8:2 weight ratio) and dissolved at 130° C. while stirred by a magnetic stirrer for two hours to obtain a solution.
(Fixation of the PVA hydrogel to the porous alumina ceramics)

Cyanic acrylate (instantaneous adhesive) was carried via infiltration and fixation beforehand at about half of the entire length of a cylindrical alumina ceramic body (porosity 40%) measuring 5 cm in diameter and 10 cm in height. The ceramic body was then immersed in the above-mentioned PVA solution and the PVA solution was carried via infiltration in the alumina ceramic body by removing gas from the ceramic body by using an aspirator. The ceramic body was then left for 24 hours in a freezer at −20° C. to set the PVA to gel. As a result, the PVA gel was carried by fixation in the alumina ceramics.
(Heat treatment of the PVA hydrogel)

To remove infiltrated and fixed cyanic acrylate and DMSO (solvent) from the above-mentioned alumina ceramics/PVA hydrogel composite body, the composite body was cleaned in acetone at 50° C. for three hours. The composite body was then dried for 24 hours at room temperature by wind and with a vacuum drier. The dried PVA hydrogel was heat-treated in silicone oil at 140° C. for one hour to obtain PVA hydrogel with low water content.

This PVA hydrogel was immersed in water at 37° C. for three days to obtain an equilibrium condition. The saturated water content rate of the obtained gel was about 20 weight %,
(The shearing and peeling strength of the PVA hydro gel)

The shearing and peeling strength of the alumina ceramics/PVA hydrogel composite body was about 3 MPa when measured with the S-100 Auto-graph made by Shimazu Seisakusho Ltd.
(Embedding the cartilage into the knee joint of a rabbit)

The PVA hydrogel artificial articular cartilage made as described above was cut and formed into a cylinder of 4 mm in diameter and 4 mm in height. The knee joint of a rabbit was unfolded by cutting the para-patellar median patella skin under "Nembutal" intravenous anesthesia. The femoropopliteus surface was drilled to the subchondral bone. The above-mentioned artificial articular cartilage was then embedded into the obtained hole.

As a comparison example, an ultra-polymer polyethylene piece (HDPE) used at the socket section of the currently used artificial articular cartilage was also embedded in the same way. Three rabbits were used for each material.

Two weeks after operation, no inflammation was found at the degenerated synovial membrane of the cartilage of all groups. In histology, immature scar tissue was generated and a few inflammation cells were found partially. However, the degree of the inflammatory cellular infiltration was low for both materials. Significant differences were not recognized between the two materials.

Four weeks after tile operation, inflammation reaction disappeared from around the materials and the maturity of the scar tissue was recognized.

Eight weeks after the operation, the maturity of the scar tissue made gradual progress for all materials. In the case of the artificial articular cartilage made of PVA hydrogel fixed alumina ceramics, bone ossification occurred at the portions of the alumina ceramics with unfixed PVA hydrogel, and the ossificated bone was firmly fixed to the joint. On the other hand, the artificial articular cartilage made of HDPE dropped easily from the joint.

The artificial articular cartilage of the first invention has the superior dynamic characteristics equivalent to those of the articular cartilage of the living body, that is, the characteristics similar to the lubrication and shock absorbing characteristics. In addition, the artificial articular cartilage can assure firm fixation to the bones of the living body. Consequently, the artificial articular cartilage can be used as the cartilage of the knee joints and coxae. Therefore, since the artificial articular cartilage has the excellent joint characteristics inherent to the living body, it is greatly beneficial to the welfare of the human being.

Example 2

(Corresponding to the second invention)

PVA with a polymerization rate of 11,000 and a saponification rate of 99.9 mol % was added to dimethyl sulfoxide (DMSO)/water mixture solvent (8:2 weight ratio) to set the PVA concentration to 5 weight %. The PVA solution was then dissolved and prepared in a constant-temperature oil bath (including ethylene glycol) at 135° C. for seven hours while being stirred by an electric stirrer.

The PVA solution used in this case should have a saponification rate of 95 mol % or more, preferably 97 mol % or more. If the saponification rate is less than the above-mentioned values, the gel to be obtained has less strength. The average polymerization rate should be 1700 or more at the average viscosity, preferably 5000 or more. If the rate is less than the values, the polymerization rate of the PVA lowers and the gel to be obtained has less strength. The starting material of the PVA should be used after molecular distillation to prevent PVA with low molecular weight from eluting.

When the PVA solution is obtained, only water can be used as solvent. However, just as in the case of the first invention, it is possible to use one or a mixture of two or more solvents described before and listed as follows: dimethyl sulfoxide (DMSO), ethylene glycol (EG), glycerol (GC), propylene alcohol (POH), ethyl alcohol (EOH), 1,3-dimethyl-imidazolizinone (DMI).

Just like the first invention, it is preferable to select DMSO from among the above-mentioned organic solvents by considering the solubility to the PVA, the ratio of mixture with water and the drop of the freezing point.

The mixture ratio between water and the above-mentioned solvent can be determined as desired, but normally should be in the range of 5:95 to 95:5.

Its concentration should be in the range of 2 to 30 weight % depending on the desired strength and water content. To prepare and adjust such a solution, PVA is generally heated and dissolved. Only heating while stirring is passable or dissolution is possible by using an auto-clave or a microwave oven.

Two pieces of rectangular-column pure titanium fiber mesh (porosity about 50%) measuring 20×20×8 mm were preformed. One piece of the pure titanium fiber mesh was set on the bottom of a metal mold (prepared separately) and the adjusted PVA solution was poured into the mold. The PVA solution was covered with the other piece of the pure titanium fiber mesh. Immediately after compression by using a press molding machine took place on the laminate, the temperature of the PVA solution was lowered by using an instantaneous cooling spray to carry PVA hydrogel via infiltration only in the desired portions inside the upper and lower fiber mesh popes. In this case, cyanic acrylate or gelatin can be filled beforehand in the portions where biologic fixation due to ingrowth and ossification of the living body tissue is desired, to carry the PVA hydrogel via infiltration and fixation only at the desired portions so that the PVA solution can be carried via infiltrated after solidification. At this time, the PVA solution which is not carried via infiltration into the above-mentioned fiber mesh can exist independently between the upper and lower fiber mesh bodies.

The pieces of the mesh bodies were then left 24 hours in a freezer at −20° C. to set the PVA solution to gel. The PVA hydrogel in the Upper and the lower pure titanium fiber mesh bodies is fixed to obtain a block of tile PVA hydrogel. In this case, the solution is set to gel in a shorter period of time as the temperature is lower. Therefore, a freezer was used at a temperature of −10° C. or less, preferably −20° C. or less. The amount of the PVA solution should be determined beforehand so that the PVA block with a desired thickness can be formed.

To remove DMSO which was used as a solvent, two pieces of the pure titanium fiber mesh/PVA hydrogel block composite bodies were infiltrated in ethyl alcohol and cleaned about-one week while heating and stirring. The pieces of the composite bodies were then dried for three days at room temperature by wind and with a vacuum drier. The dried composite bodies were heat-treated in silicone oil at 140° C. for three hours. This heat treatment process can be done in the air, but preferably be conducted in vacuum, nitrogen gas flow or silicone oil. The heat treatment temperature should be 100° C. or more where the crystallization of the PVA can be promoted, preferably in the range of 100° to 180° C. The sufficient heat treatment time is generally 1 to 72 hours depending on the heat treatment temperature. The time can be made longer.

In the end, the pieces of the composite bodies were immersed in waiter. In this way, the two artificial intervertebral discs were obtained which were similar in shape to that shown in FIG. 2 and were composed of the pure titanium fiber mesh body and PVA hydrogel block.

Figure 2:
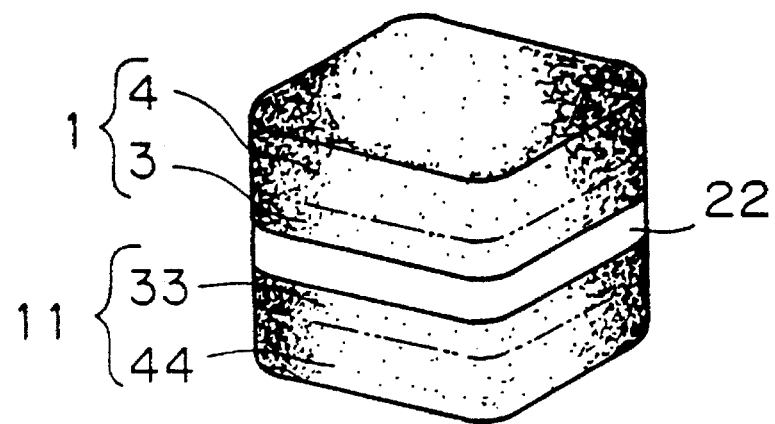
FIG. 2 is a schematic view illustrating the artificial intervertebral disc produced as an example of the second invention.

FIGS. 2 and 3 are schematic views of artificial intervertebral discs of the second invention. In the figures, numerals 1 and 11 represent pure titanium fiber mesh bodies positioned over and under the artificial intervertebral disc. Numeral 22 represents a PVA hydrogel block. Numerals 3 and 33 represent PVA hydrogel infiltration portions of the pure titanium fiber mesh bodies. While numerals 4 and 44 represent the hydrogel non-infiltration portions.

The pure titanium fiber mesh bodies 1 and 11 were firmly connected and fixed in the condition where the PVA hydrogel from the PVA hydrogel block 22 had entered via infiltration part or most of the block 22. In this case, to make the connection firmer, a collar or a projection (both not shown) can be provided at the ends of the PVA hydrogel infiltration portions 3 and 33 so that an anchoring effect is offered.

Figure 3A:
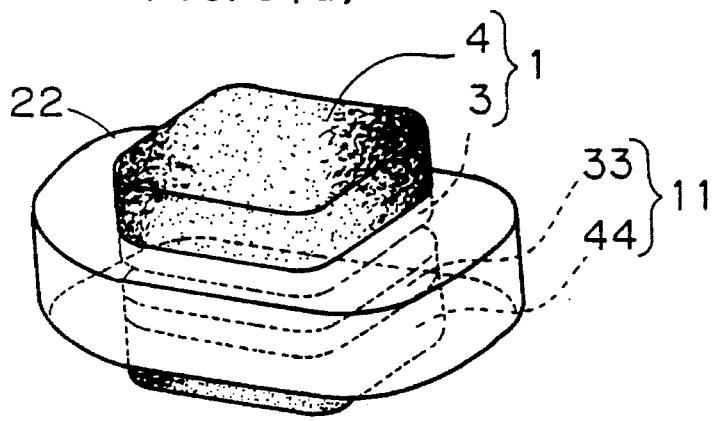
FIGS. 3(a) to 3(e) are schematic views illustrating the artificial intervertebral discs of examples of the second invention.
Figure 3B:
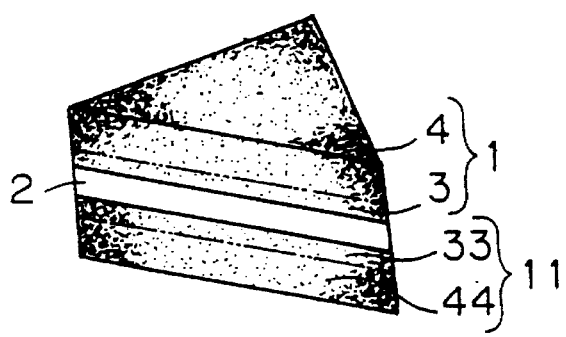
Figure 3C:
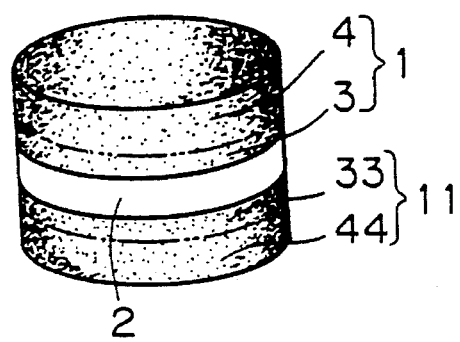
Figure 3D:
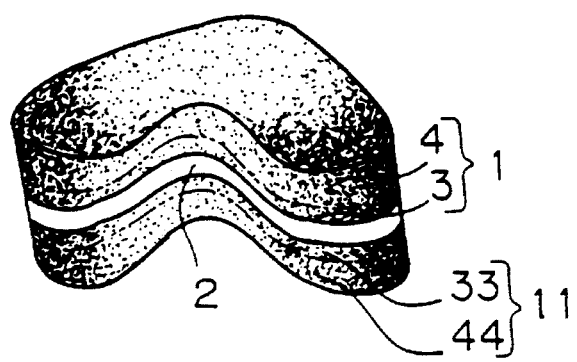
Figure 3E:
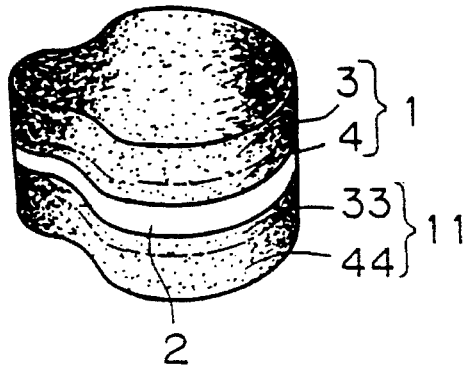

Like the artificial intervertebral disc shown in FIG. 3(a), the block 22 made of the PVA hydrogel has wing sections projecting right-and-left or back-and-forth to provide a larger area for contacting the end plates of the upper and lower neighboring vertebral bodies, thereby allowing such load distribution as can be obtained by the intervertebral disc of the living body. The block 22 is desired to have an anatomical sectional shape close to the end plate to enhance the internal stability of the artificial intervertebral disc when installed. The shape of the artificial intervertebral disc of the second invention is not limited to a rectangular column, but can have a shape of a triangular column, an elliptic cylinder, a circular cylinder or an irregular shape depending on the shape of the installation position, as shown in the schematic views of FIGS. 3(b) to 3(e). The above-mentioned titanium fiber mesh bodies 1 and 11 can be composed of porous ceramic bodies, metallic mesh bodies or metallic porous bodies such as metallic beads, which are affinitive to the living body. In this case, the porous body of the second invention can be made of alumina, zirconia, hydroxy apatite or crystallized glass ceramics. The metallic porous body can be made of titanium-based alloy, cobalt-chrome alloy or stainless steel, which are affinitive to the living body. Furthermore, the above-mentioned pure titanium fiber mesh bodies 1 and 11 can be a combination of ceramic or metallic porous bodies described above. The porosity of the porous bodies is desired to be in the range of 20 to 90%. In the example of the second invention, two porous bodies are provided over and under the above-mentioned block. However, porous bodies provided back-and-forth and right-and-left as stoppers and integrated with the above-mentioned block can also be used. Accordingly, the number of porous bodies of the artificial intervertebral disc of the second invention is not limited to two.

The water content of the PVA hydrogel of the porous body/PVA hydrogel block composite body made by infiltrating water in the end can be changed greatly in the range of 10 to 80 weight % depending on the heat treatment condition of the composite body so that the water content suited for the desired dynamic characteristics can be adjusted and obtained. When this artificial intervertebral disc was immersed in water at 37° C. for a week until its equilibrium condition was obtained, the saturated water content of the block made of the PVA hydrogel was about 14 weight %.

Figure 4:
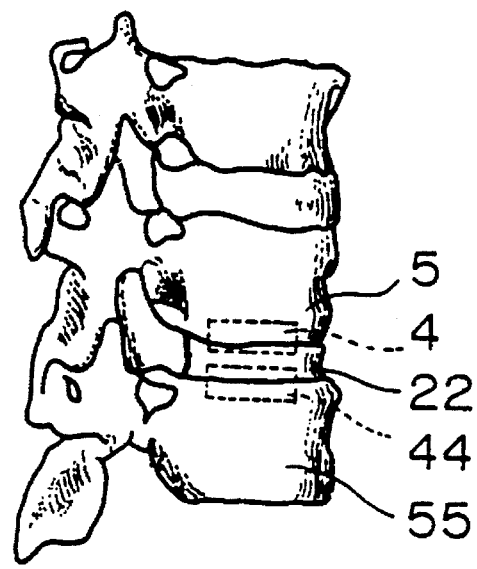
FIG. 4 is a view illustrating the installation condition of the artificial intervertebral disc of the second invention inside the human body.

FIG. 4 shows an actual installation condition of the artificial intervertebral disc of the second invention which is similar to that shown in FIG. 3(a). In this case, the non-infiltration portions 4 and 44 of the PVA hydrogel of the pure titanium fiber mesh bodies 1 and 11 directly contact the bones of the upper and lower vertebral bodies 5 and 55, thereby achieving biological fixation by ingrowth and ossification of bones into the porous interior of the non-infiltration portion mentioned above.

Next, some experiments were conducted to examine the characteristics of the artificial intervertebral disc of the second invention produced by the above-mentioned method.

Experiment 1

Figure 5A:
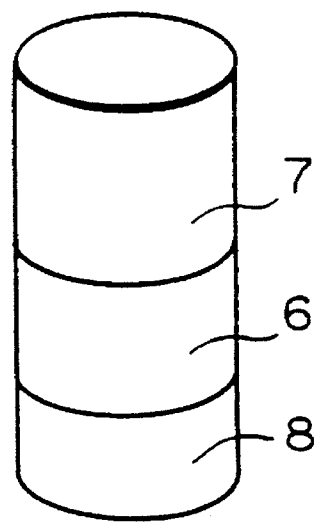
FIG. 5(a) is a view illustrating a PVA hydrogel model of an example of the second invention and FIG. 5(b) is a view illustrating an ultra-polymer polyethylene model of an example of the second invention.
Figure 5B:
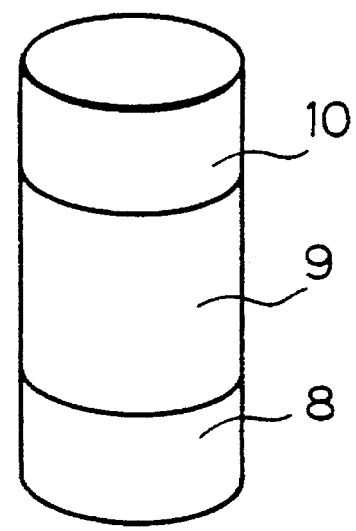

A PVA solution of 4 weight % was prepared and adjusted by using the preparation method for the above-mentioned artificial intervertebral disc and a circular cylindrical PVA hydrogel 6 measuring 6 mm in diameter and 3 mm in height was made [FIG. 5(a)]. The water content of the gel was about 16 weight %. FIG. 5(a) shows a PVA hydrogel model sample made by laminating a circular cylindrical pure titanium fiber mesh body 7 (porosity about 50%) measuring 6 mm in diameter and 6 mm in height and cancellous bone section 8 obtained from the knee joint of a pig and formed in a circular cylinder measuring 6 mm in diameter and 3 mm in height over and under the above-mentioned PVA hydrogel block 6. FIG. 5(b) shows an ultra-polymer polyethylene model sample made by laminating an ultra-polymer polyethylene body 9 (6 mm in diameter and 5 mm in height, a bone cement piece made of polymethyl methacrylate 10 (6 mm in diameter and 4 mm in height) and the above-mentioned cancellous bone section 8 (6 mm in diameter and 3 mm in height).

Figure 6:
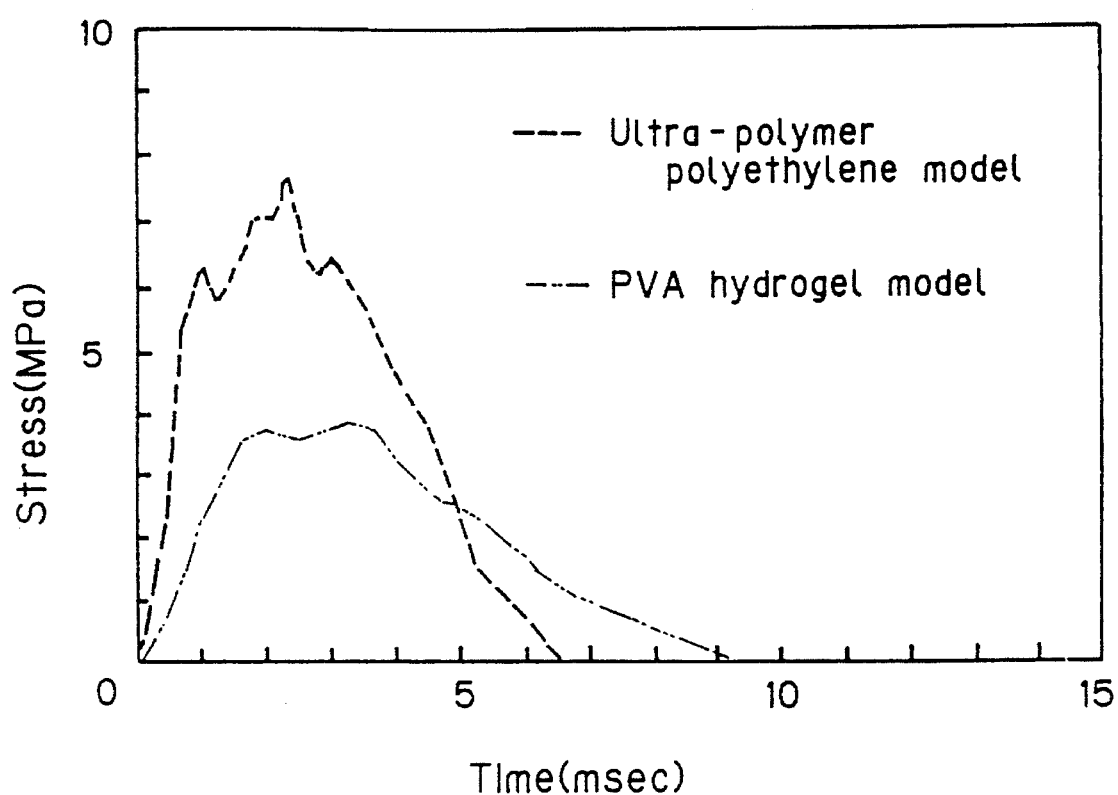
FIG. 6 is a graph illustrating secular changes in the stresses obtained during experiment 1 using the examples of the second invention.

A weight of 2.7 kg was dropped from a height of 50 mm to each sample in physiological saline solution. The stress transmitted through each sample was measured with the passage of time by using a load cell installed under each sample. FIG. 6 shows the results of the measurement. According to the graph, a shock load was transmitted for an extended period of time in the case of the PVA hydrogel model sample. It was thus confirmed that the PVA hydrogel model sample was superior in shock absorbing performance.

Experiment 2

Just as in the case of the first experiment, a PVA solution of 4 weight % was prepared and adjusted. Four pieces of circular cylindrical pure titanium fiber mesh bodies measuring 8 mm in diameter and 20 mm in height with porosity values of 50 and 70% (two pieces for each type) were also produced. Cyanic acrylate was infiltrated and fixed in the section at about half length of each piece. The PVA solution was pressed and infiltrated by using an injection syringe. The following treatment methods were the same as those for the first invention, except that heating and cleaning in acetone were added before cleaning in ethyl alcohol to remove infiltrated and fixed cyanic acrylate. Just as in the case of the first invention, the pure titanium fiber mesh/PVA hydrogel block composite bodies were made. The water content of the block comprising the PVA hydrogel was about 18 weight % just as in the case of experiment 1.

The PVA hydrogel block composite bodies were trimmed in a size of 5 to 6 mm in diameter and subjected to a shearing force test by using an auto-graph universal tester made by Shimazu Seisakusho Ltd. Table 1 shows the results of the measurement.

TABLE 1

| Sample | Test factor | | |
|---|---|---|---|
| | Contact area (mm$^2$) | Load (kgf) | Shearing stress MPa |
| Sample 1 (porosity 50%) | 24 | 3.5 | 1.4 |
| Sample 2 (porosity 50%) | 20 | 3.2 | 1.6 |
| Sample 3 (porosity 70%) | 28 | 6.1 | 2.1 |
| Sample 4 (porosity 70%) | 28 | 5.4 | 1.9 |

The average shearing stress of the composite bodies with 50% porosity was 1.5 MPa and that of the composite bodies with 70% porosity was 2.0 MPa. The composite bodies with higher porosity delivered higher shearing stress. Since the maximum shearing force applied to the thoractic and lumber vertebrae of a human being is said to be 150N, it is assumed that at least the maximum shearing force of 0.375 MPa is applied to the connection area (20×20=400 mm$^2$) of the pure titanium fiber mesh/PVA hydrogel block composite body of example 1. It is clear that the shearing forces of the composite bodies of the present example are far greater than the maximum value. Therefore, it is proved that in the artificial intervertebral disc of the second invention, the connection between the PVA hydrogel block 22 and porous bodies can be firmly secured via infiltration and fixation in part or most of the pores of the ceramic or metallic porous bodies positioned over and under the PVA hydrogel block 22.

Experiment 3

A PVA solution of 4 weight % was prepared and adjusted by the above-mentioned production method of the artificial intervertebral disc of the second invention. Pure titanium fiber mesh/PVA hydrogel block composite bodies (water content about 18 weight %) were made by using a circular cylindrical pure titanium fiber mesh body measuring 5 mm in diameter and 10 mm in height and with 70% porosity. The composite bodies were embedded in the pateliar groove of the femurs of mongrel dogs. They were killed with the passage of time and the operation sections were examined histologically.

Two weeks after the operation, immature scar tissue was generated and a few inflammation cells were found partially. However, the degree of infiltration was low. Four weeks after the operation, the inflammation reaction around the sample disappeared. As the scar tissue became matured, the ingrowth of new bones into the pores of the pure titanium fiber mesh body was recognized. The new bone trabeculation became matured with the passage of time. Eight weeks after the operation, the composite body was firmly fixed to the base of the bone. Therefore, it was proved that the fixation to the living tissue was achieved by the ossification of the living tissue to the hydrogel non-infiltration portions of the porous body located over and under the PVA hydrogel block, and the dynamic stability and affinity to the living body were made excellent for an extended period of time.

In the end, an experiment similar to experiment 3 was conducted by using porous bodies made of alumina measuring 5 mm in diameter and 10 mm in height and with 70% porosity. The results of the experiment were excellent just like those of the above-mentioned experiment results.

The artificial intervertebral disc of the second invention has characteristics similar to the dynamic characteristics: flexibility and shock absorbing characteristics of the living body. In addition, it offers firm connection and fixation to living bones. Its composite body has high connection strength applicable to actual use. Therefore, the disc can be used as am artificial intervertebral disc which is an important element of the spine. The disc can thus substitute for the excellent intervertebral disc of the living body, thereby greatly contributing to the welfare of human being.

The above descriptions are made of the first and second inventions directed to an artificial cartilage and artificial intervertebral discs. However, it could be understood from the above descriptions that the present prosthesis is also applicable to a prosthesis for replacement of damaged living bones.

We claim:

1. A prosthesis used for replacing at least one of a damaged bone, an articular cartilage and an intervertebral disc, the prosthesis comprising:

polyvinyl alcohol hydrogel and a porous body, the porous body comprising at least one of a ceramic material and a metallic material, wherein the hydrogel is carried into the porous body via infiltration and fixation, thereby forming a resulting porous body having a shape corresponding to the at least one of a damaged bone, an articular cartilage and an intervertebral disc it replaces, and wherein the resulting porous body is positioned at and brought into contact with articular bone portions so that bone tissue is allowed to grow into and ossify within the resulting porous body to connect the hydrogel to bone portions of a living body.

2. The prosthesis of claim 1, comprising:

a pair of porous bodies, the pair of porous bodies comprising at least one of a pair of metallic bodies and a pair of ceramic bodies, and a polyvinyl alcohol hydrogel block integrally incorporated between the pair of porous bodies.

3. The prosthesis of claim 2, wherein the polyvinyl alcohol hydrogel is carried by the porous body contacting the hydrogel block via infiltration and fixation.

* * * * *

UNITED STATES PATENT AND TRADEMARK OFFICE
CERTIFICATE OF CORRECTION

PATENT NO. : 5,458,643

DATED : October 17, 1995

INVENTOR(S) : Masanori OKA, Shokyu GEN, Yoshito IKADA, Hideaki OKIMATSU

It is certified that error appears in the above-identified patent and that said Letters Patent is hereby corrected as shown below:

Column 4, line 41, change "dimethyl glycol (DMSO)" to -- DMSO --.

Signed and Sealed this

Eleventh Day of February, 1997

Attest:

BRUCE LEHMAN

Attesting Officer

Commissioner of Patents and Trademarks